United States Patent [19]

Timme

[11] Patent Number: 4,694,839
[45] Date of Patent: Sep. 22, 1987

[54] AUXILIARY STIMULATION APPARATUS FOR APNEA DISTRESS

[76] Inventor: William F. Timme, 891 Amaryllis Ave., Oradell, N.J. 07649

[21] Appl. No.: 842,831
[22] Filed: Mar. 24, 1986
[51] Int. Cl.⁴ ............................................. A61B 5/08
[52] U.S. Cl. ...................................... 128/721; 128/41
[58] Field of Search ....................... 128/41, 44, 46, 56, 128/582, 720, 721

[56] References Cited

U.S. PATENT DOCUMENTS

| | | | |
|---|---|---|---|
| 1,634,373 | 7/1927 | Mann | 128/41 |
| 3,310,050 | 3/1967 | Goldfarb | 128/41 |
| 3,323,517 | 6/1967 | Keller | 128/41 |
| 3,373,739 | 3/1968 | Rankin | 128/56 |
| 3,547,106 | 12/1970 | Bornman | 128/721 |
| 3,552,388 | 1/1971 | Zelenka | 128/56 |
| 3,612,043 | 10/1971 | Inaki | 128/582 |
| 3,658,052 | 4/1972 | Alter | 128/721 |
| 3,730,173 | 5/1973 | Beaton | 128/720 |
| 3,888,242 | 6/1975 | Harnz et al. | 128/582 |
| 3,950,799 | 4/1976 | Frank | 128/721 |

Primary Examiner—William E. Kamm
Assistant Examiner—Max F. Hindenburg
Attorney, Agent, or Firm—Ralph R. Roberts

[57] ABSTRACT

This invention provides an assist to a monitor for apnea of infants and very young children. Monitors for such problems are well known, but the usual signals from these monitors are flashing lights or audible sounds. These signals from the monitor may be unobserved or not responded to by an attendant. The present assist apparatus is provided so that the patient is stimulated at the first actuation from the monitor. There are two areas of the patient receptive to such stimulation; a first area is the sole of a foot and the other area is at the neck. At the foot, a shoe is provided with a motor or reciprocated plunger to vibrate or lightly engage the skin of the patient. At the neck area, a removable collar with motors or reciprocating plunger is provided to lightly engage the skin of a patient. Either separately or in combination, the patient is stimulated to an aroused condition absent an attendant. Electrical energy or pressurized air may be utilized.

19 Claims, 14 Drawing Figures

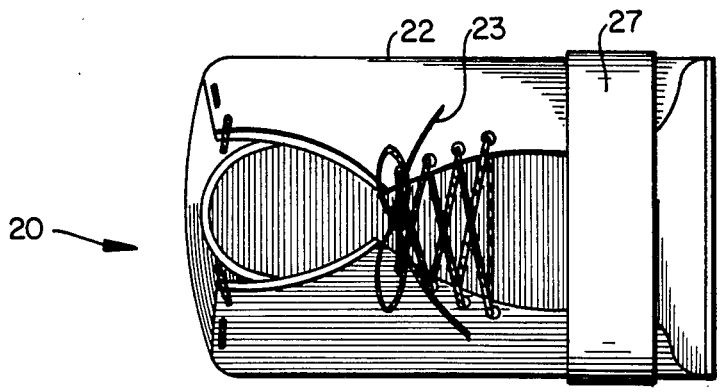
Fig. IA
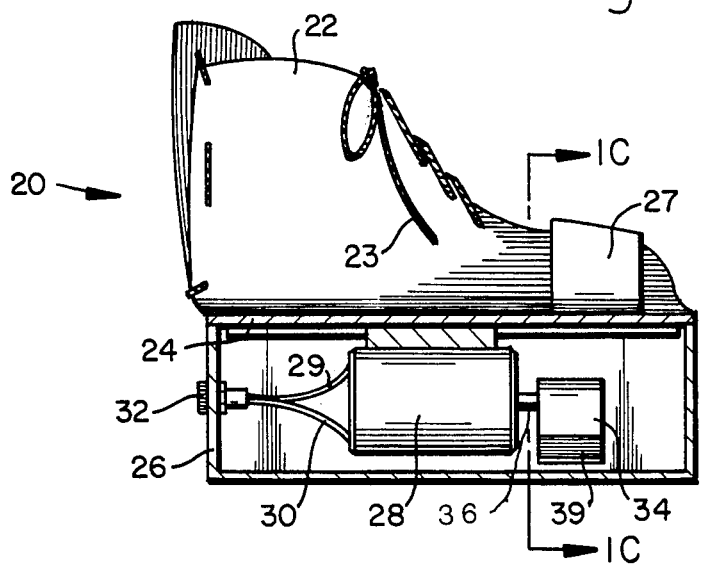
Fig. IB
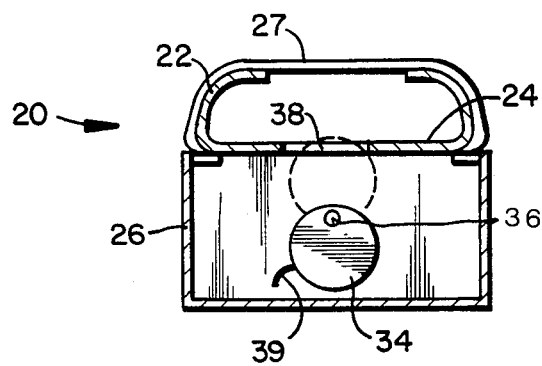
Fig. IC

AUXILIARY STIMULATION APPARATUS FOR APNEA DISTRESS

BACKGROUND OF THE INVENTION

1. Field of the Invention

With respect to the classification of art as established in and by the United States Patent Office, this invention pertains to monitoring and auxiliary stimulation of the breathing of infants and young children suspected to be subject to apnea. Monitoring apparatus is well known, but visual and noise alarms do not always bring a response. The present invention provides an auxiliary response to stimulate and waken the infant being monitored.

2. Description of the Prior Art

A careful pre-Ex search in the art was made and included in the many patents in this field were monitoring and auxiliary means as follows: U.S. Pat. No. 2,776,658 to GIBBON, as issued Jan. 8, 1957. This patent shows a rocking bed apparatus, but no auxiliary means to stimulate an infant whose respiratory rhythm changes and is cause for alarm. An auxiliary stimulator is provided by U.S. Pat. No. 3,730,173 to DEATON, as issued May 1, 1973. This shows electronic signals derived from the monitoring device with the foot of the patient receiving a directed "stream of pressurized fluid (air) against a portion of the patient's body (foot) to provide cutaneous stimulation thereto." The instant device provided by the Applicant is a motorized or vibrated and gently striking member that lightly contacts the patient's sole of the foot and/or neck in response to the alarm being activated.

Also found in this search was U.S. Pat. No. 3,831,586 to PETIT, as issued Aug. 27, 1974, and involves a monitor of the respiration of a patient and provides an illuminating signal. There is no additional auxiliary device actuated in response to the monitor signal. A U.S. Pat. No. 3,950,799 to FRANK, as issued Apr. 20, 1976, shows a monitor whose alarm causes a pillow device to be actuated and provide "momentary inflation of a pneumatic means adapted for placement under a patient to raise the patient and induce loss of equilibrium for startling the patient from a natural respiratory respiration pattern." The device of this application is effective only after monitor signals are sent and then only to startle the patient into an awake condition whereat and whereby the awake condition increases the degree and speed of respiratory movement. Also noted were U.S. Pat. No. 4,146,885 to LAWSON, Jr., as issued Mar. 27, 1979, which is another alarm device, but shows no auxiliary means for inducing a response for increased breathing. Also noted was U.S. Pat. No. 4,438,771 to FRIESEN et al, as issued Mar. 27, 1984, which, like the prior patent to LAWSON, uses a pneumatic mattress arrangement to provide a monitor rather than an auxiliary means to induce an increase in respiratory actuation.

It is important to carefully monitor certain physical characteristics or physiological parameters of certain hospital patients. Small, premature infants are often subject to transient cessation of respiration, termed apnea. Additionally, the condition of infant patients having heart conditions must be monitored carefully to detect variations in the heart rate. A number of different types of monitoring techniques have been heretofore developed to monitor these and other physiological parameters, as for example, impedance pneumography commonly used to monitor respiratory changes.

Many prior monitoring devices have relied upon a visual or audible alarm which is actuated upon the detection of the physiological parameter variations, after which a nurse or doctor must initiate emergency treatment. Such treatment often comprises, especially in the case of premature infants, cutaneous stimulation by thumping or pinching the patient's body.

The cessation of respiration, or the inability to get one's breath referred to as apnea, is a serious problem which becomes dangerous especially in premature infants where such occurrences are frequent. It is understood that repeated attacks as well as prolonged attacks of apnea are factors which carry a poor prognosis both for life and for subsequent mental development resulting from irreversible cerebral damage sustained during these apneic episodes. The best prospect of reducing harmful effects of lateoccurring apnea is through constant surveillance, preferably using some automated device to alert attendants so that stimulation through resuscitation can begin promptly. As a consequence, apnea monitoring of premature infants has become an accepted practice in most institutions.

Upon detection of an apnea episode, a visual or audible alarm is generated to call the attending nurse for prompt manual stimulation of the infant in an attempt to terminate the episode by restoring normal breathing. Alertness and responsiveness of the nursing staff is important as it becomes more difficult to obtain a positive response to stimulation the longer the apnea persists. Naturally then, most apnea monitors are designed to provide an early alarm. Unfortunately, however, most of these apnea episodes are of a short duration and occur almost randomly during any day of neonatal life. Thus, they place an unnecessary burden on the nurse to the extent that in some cases it is conceivable that the alarms may even be neglected.

The purpose of the present invention is to avoid some of the problems incurred in apnea monitoring by early stimulation of the respiratory distressed patient. The preferred innovative technique of automatic mechanical stimulation in the present embodiment is directed to suddenly startle the infant into a natural respiration pattern.

SUMMARY OF THE INVENTION

This invention may be summarized, at least in part, with reference to its objects. It is an object of this invention to provide, and it does provide, an auxiliary device or devices for impinging on the skin of a patient stimulation sufficient to cause the patient to awaken or to become more active.

It is a further object to provide, and it does provide, auxiliary stimulation devices that gently strike the patient's skin to cause arousal and an increase of movement. This stimulation is activated in response to a monitor alarm signal and with application to the skin areas of a foot and neck area of a patient.

In brief, this invention and apparatus proposes to use known monitoring apparatus and signal means produced therefrom. In the disclosed apparatus there are two areas in which stimulation is applied to the skin of a patient. These areas are a sole of a foot of the patient and two areas of the neck of a patient. Stimulation is through electric motor means that rotates an eccentric disc to lightly strike the skin or may have flexible beating portions that provide light flail actuation and striking. There is also contemplated a reciprocating striking device actuated by compressed air.

The auxiliary unit for the sole of the foot is a shoe that can be tied to the foot of an infant. This shoe has a box-like member at the sole area and within this enclosure is an electric motor carrying on its output shaft an eccentric disc. This disc when and while rotated strikes the sole area or alternately a small aperture may be made in the sole area and a flail portion may be caused to strike the sole of the foot of a patient. Rather than a revolving disc, there may be a reciprocated plunger device that gently strikes the foot at the sole area. This removably attachable shoe member is used only when monitoring the patient and is not present at other times.

The apparatus for the neck area of a patient is, more or less, U-shaped, although the intermediate collar portion is flexible and may have a tie string to cause the neck device to be placed and secured around the neck of the patient. It is contemplated that motors be secured at each end of the collar portion and, when activated, rotate an eccentric portion. A flexible flail device may be secured with and be rotated with each eccentric disc. The motors for this auxiliary means may be either electric or pneumatic.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there has been chosen a specific embodiment of auxiliary stimulation apparatus for apnea distress as adopted for use with existing patient monitoring apparatus and showing a preferred means for construction of the auxiliary devices. This specific embodiment and an alternate embodiment have been chosen for the purposes of illustration and description as shown in the accompanying drawings wherein:

BRIEF DESCRIPTION OF THE DRAWINGS

FIGS. 1A, 1B and 1C represent plan, side and sectional views of an infant's shoe having a motor means to induce stimulation to an infant or young child, FIG. 1B shown partly in section and diagrammatic so as to illustrate the arrangement of the major elements, and FIG. 1C a sectional view, also diagrammatic, and taken on the line 1C—1C of FIG. 1B and looking in the direction of the arrows;

In the following description and in the claims, various details are identified by specific names for convenience. These names are intended to be generic in their application. Corresponding reference characters refer to like members throughout the several figures of the drawings.

Figure 2:
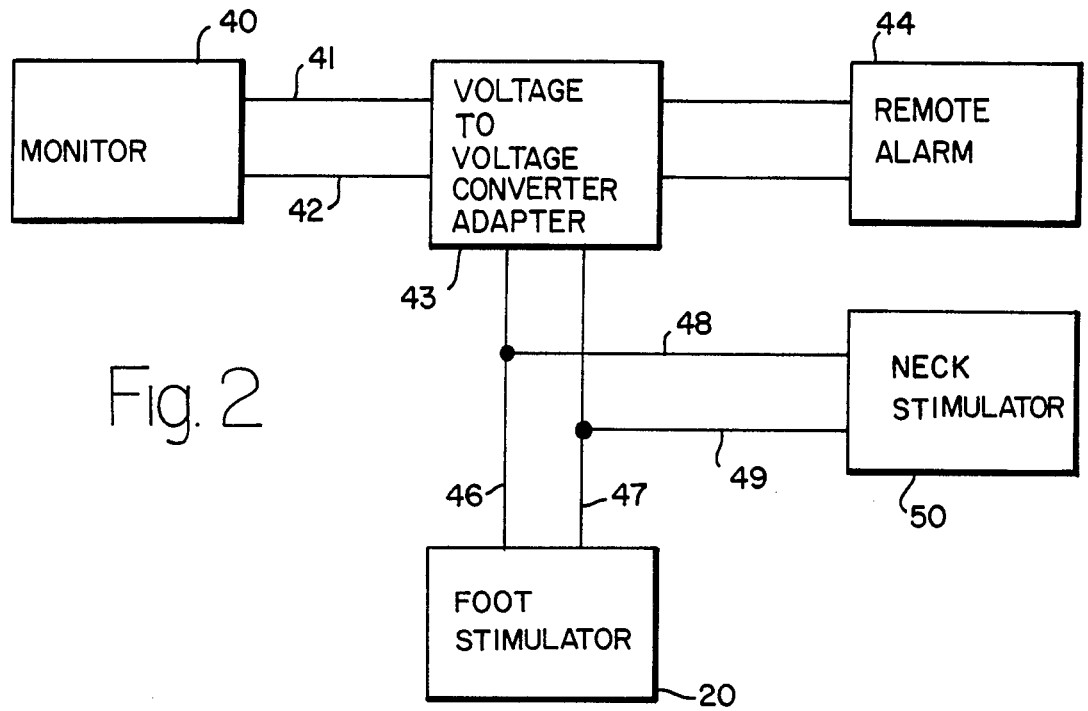
FIG. 2 represents a schematic view of a circuit diagram for the conversion of electrical signals from a monitor to a voltage conversion adapter to actuate foot and neck stimulation.

The drawings accompanying, and forming part of, this specification disclose details of construction for the purpose of explanation, but structural details may be modified without departure from the concept and principles of the invention and the invention may be incorporated in other structural forms than shown.

DESCRIPTION OF THE EMBODIMENT OF FIGS. 1A, B AND C

Referring now to the drawings and the embodiments therein, a foot stimulation device is shown in FIGS. 1A, 1B and 1C and, as an assembly, is identified as 20, and includes a shoe 22 sized to be mounted on and removably secured to a foot of an infant as by a lace 23. This shoe has a sole portion 24 to which is attached a protective enclosure 26. A strap 27 is shown as securing the fore portion of the shoe 22 to the sole member 24. This is a matter of preference and design. Within this enclosure is carried a motor 28 actuated by voltage supplied through wires 29 and 30 and terminating at a connector 32. An eccentric disc 34 is carried on rotor shaft 36 of the motor. This eccentric disc 34 may be arranged to lightly strike the sole 24 and induce vibrations or, if desired, the sole 24 may have an aperture 38, as seen in FIG. 1C, and a flexible flail 39 in the nature of a flexible strip of cloth or plastic of a desired extent so as to swing into this aperture 38 and with the distal end of this flail lightly striking the sole of the foot of the patient to effect stimulation of the patient.

Motor 28 is shown as an electric motor with conductors 29 and 30 attached to a connector 32 to provide a convenient disconnect means. The motor may also be a pneumatic type where pressurized air for an outside source may be utilized to rotate the eccentric at a determined speed. If and when the flail 39 is to be utilized, the aperture 38 is also provided so that the patient's foot may be struck lightly.

USE AND OPERATION OF EMBODIMENT OF FIGS. 1A, B AND C

No matter the motive power to the motor, it is contemplated that the shoe 22 is of a size to be removably attached to the foot of the patient. This shoe is of a style that is easily placed on the foot of a patient and with a loosened lace 23 is adjusted to a desired position thereon, after which the shoe is secured in this desired position by tightening and tying the lace 23 in the usual manner. Power is supplied to the motor and this power is actuated when a monitor sends actuation signals to the stimulator in the shoe.

Conventionally, and in most patient care facilities as well as for home care of infants, there are two types of monitor outputs which may be encountered. The first type is a voltage output from the piezo element in the monitor. The other type of monitor is a frequency output from one speaker which then must be converted to a voltage output signal. Circuit diagrams are shown for each type of conversion.

EMBODIMENT OF FIG. 2

In FIG. 2 is diagrammatically shown a circuit diagram for actuation and using the first type of monitor output identified above. From a monitor identified as 40, electronic signals are sent by conductors 41 and 42 to a converter adapter 43 which provides a desired voltage-to-voltage conversion. From this adapter signals may be sent to a remote alarm 44, which is not further identified as this is a matter of preference. From this adapter, conductors 46 and 47 are indicated as extending to the foot stimulator 20 described above. Also connected to conductors 46 and 47 are conductors 48 and 49 which carry voltage signals to a neck stimulator device 50, to be discussed later as to function and configuration.

EMBODIMENT OF FIG. 3

Figure 3:
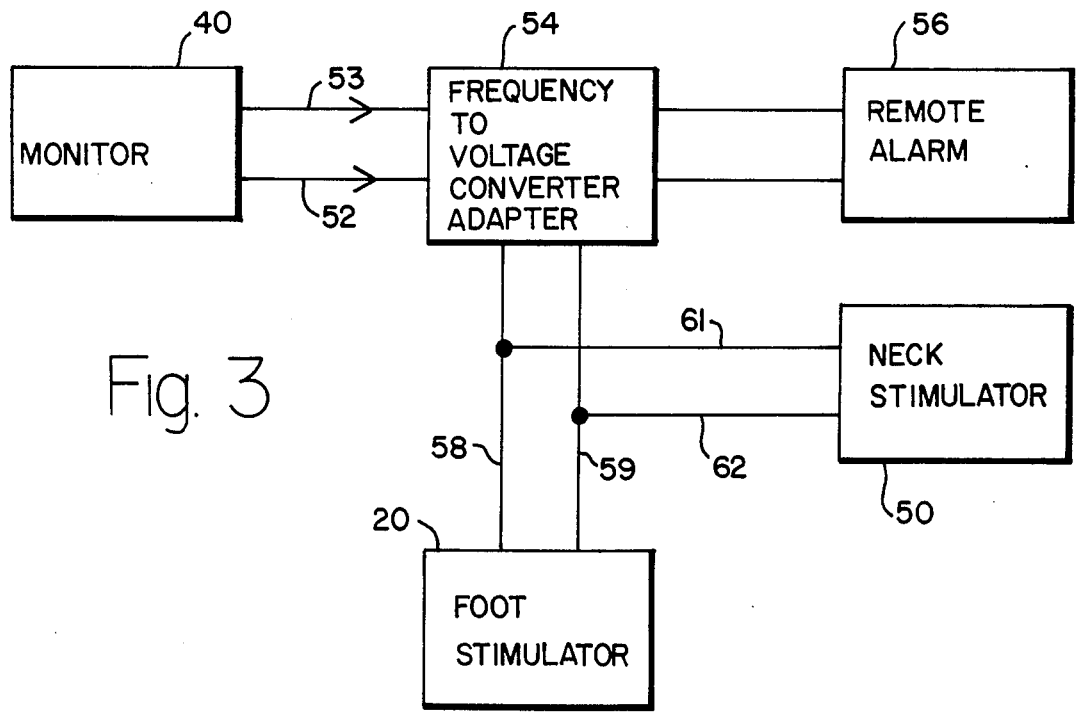
FIG. 3 represents an alternate schematic view of a circuit diagram for the conversion of audible vibrations from a monitor to a voltage converter by which electrical signals are sent to actuate foot and neck stimulations.

In FIG. 3 is diagrammatically shown a circuit diagram for actuating a monitor alarm in which frequency (usually a loudspeaker device) is produced. From a monitor 40, signals are sent, as indicated by arrows, on conductors 52 and 53 to a converter adapter 54 which is adapted to convert frequency to a voltage. The output from this converter is fed through conductors to a remote alarm 56, if desired, and not further identified. As in the diagram of FIG. 2, an output from the adapter 54 is also fed as electrical signals to conductors 58 and 59, thence to a foot stimulator 20 and through connected conductors 61 and 62 to the neck stimulator 50.

PLUG-IN ADAPTER OF FIGS. 4A AND 4B

Figures 4A, 4B:
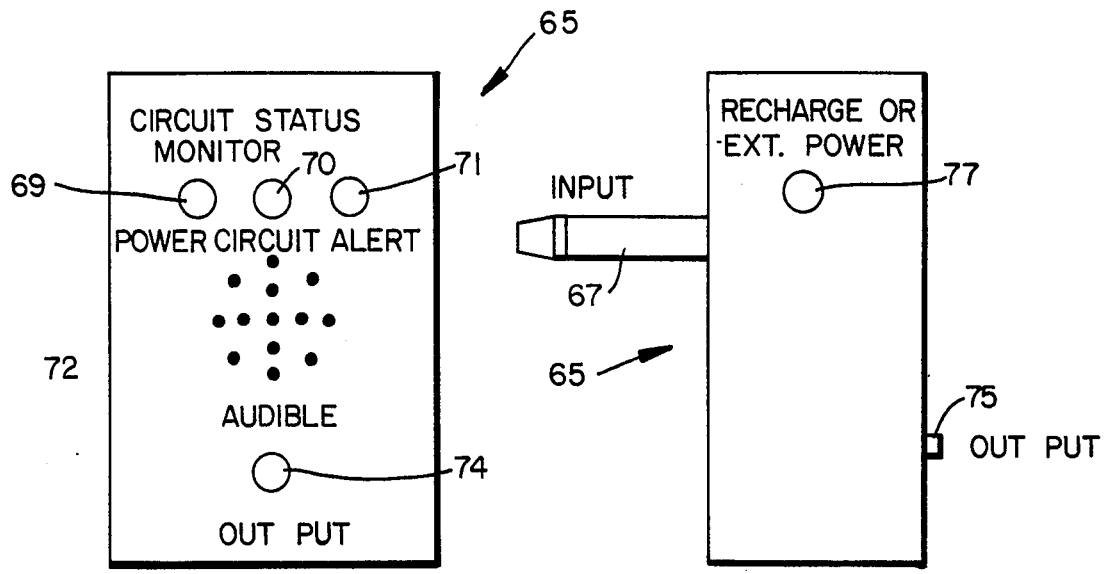
FIGS. 4A and 4B represent face and side views of a plug-in converter for the circuits of FIG. 2 or FIG. 3.
Figure 5:
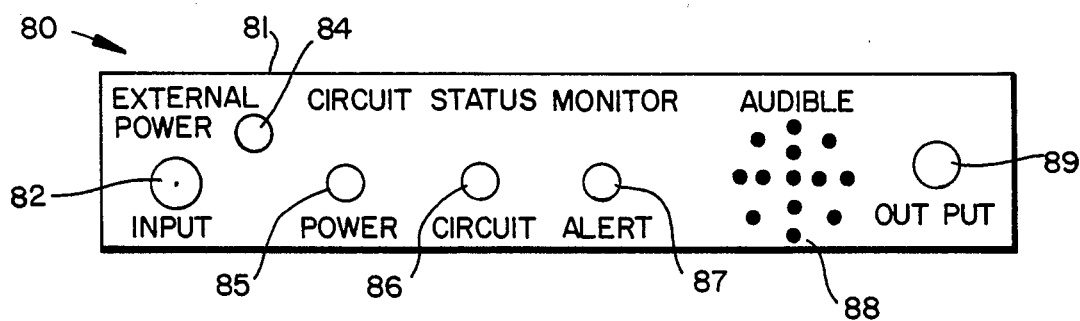
FIG. 5 represents a face or front view of a converter housing adapted for the circuit control for the stimulator means of this invention.

Circuitry and housing can be provided in many different ways, depending on the type of monitors used. The housing provided may be a plug-in type or a remote unit. As an exemplification of a plug-in type, reference is to FIGS. 4A and 4B in which a plug-in housing is generally identified as 65. In FIG. 4B, a plug input member 67 is a conventional conducting plug for two circuit conductors. In FIG. 4A there is depicted a power indicating means in the nature of an indicating lamp 69. A similar indicator 70 is illuminated when the circuit is connected and employed. A visual alert signal 71 is also indicated by an illumination means such as a lamp. Immediately below and more or less midway thereof is a multiplicity of holes for an audible signal such as a loudspeaker. These holes are indicated as 72. An output connection may be indicated at 74, with the actual output connection 75 made on the side opposite the plug input member 67. Seen in FIG. 4B is a connector 77 for a recharge or for external power as particularly provided in and with this housing.

EMBODIMENT OF FIG. 5

A housing adapter 80 is shown in this FIG. and is very similar in functional use as the plug-in adapter of FIGS. 4A and 4B, but this adapter is to be placed in a line conductor. This housing may be sized to be carried by common or on top of standard monitors. No dimensional limitations are contemplated as the housing should be sufficient for standard P. C. boards plus needed wiring or batteries which may include rechargeable batteries. As depicted, the adapter 80 includes an enclosure 81, usually of metal or plastic, and on a face portion there is depicted an input receptacle or connector 82. Signal light 84 indicates when external power is on or supplied. To the right thereof is another signal light 86 indicating to the observer that the circuit is powered. Still further to the right is a signal lamp 87 indicating to the attendant that an alert from the monitor is being made. At the same time as a visual alert is being sent, an audible signal is also provided. A speaker within the housing 81 has a plurality of small holes 88 through which developed sound may be heard. An auxiliary output 89 may include means for making this connection and/or a signal lamp that such auxiliary means is employed. This adapter 80 is merely an alternate of the plug-in device of FIGS. 4A and B, and no patentable distinction is ascribed to this configuration.

EMBODIMENT OF FIGS. 6A AND 6B

Figure 6A:
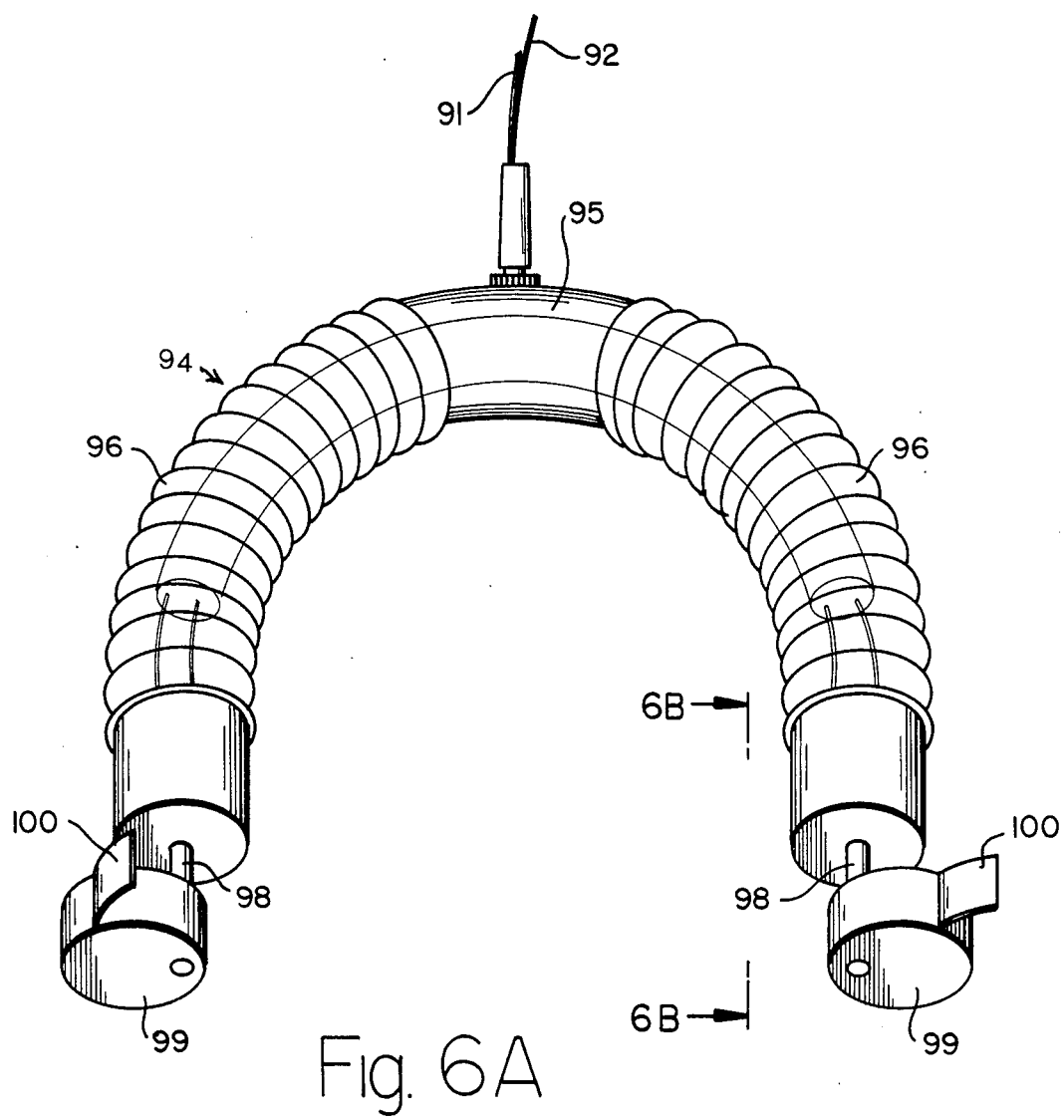
FIGS. 6A and 6B represent isometric and fragmentary side views of a neck stimulator apparatus used with a circuit as in FIG. 2 or 3, the view in FIG. 6A partly diagrammatic to illustrate stimulation apparatus for the neck portion of the patient and FIG. 6B representing a side view, partly diagrammatic, and showing a motor and eccentric disc retained in each end of the collar member.
Figure 6B:
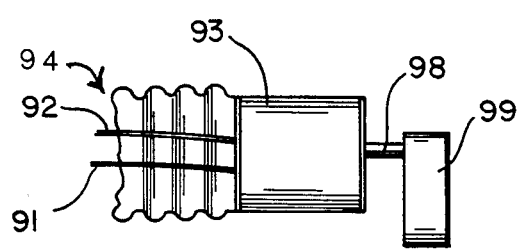

In FIGS. 6A and 6B there is shown a neck collar member, identified as 50, in the circuit diagrams of FIGS. 2 and 3. This stimulator is placed on the patient to provide stimulation to the neck areas. It has been found that many patients are sensitive near the neck and respond to vibrations or light touching of this or these areas. To insure that the infant or patient responds to the monitor signals, there is also shown this device which is also actuated. Connecting means to the converter signals is indicated in the circuit diagrams of FIGS. 2 and 3.

Electrical signals from a converter are received in and through conductors 91 and 92 and as electronic signals are carried to electrical motors 93 which are similar to or are identical to motor 34 shown in FIGS. 1B and 1C. These motors are carried in and are retained in end portions of a flexible U-shaped collar member 94. As depicted, this U-shaped portion has a fixed central portion 95 to which flexible tubular members 96 are secured. These flexible portions are contemplated to be movable to and into a desired arc. The motors 93 are each shown with an extending shaft 98 on which an eccentric disc 99 is secured. Carried by each eccentric disc is a flail 100, which is very flexible and usually is of cloth or plastic. When and as the motors 93 are actuated so as to revolve at a determined speed, the eccentrics 99 and the flail portions 100 produce vibrations and a light striking of the skin of the patient.

Not shown but contemplated is a string by which the collar member portion 94 may be loosely secured to the neck portion of the patient. Each eccentric produces vibrations and the flail portion attached thereto produces a light striking of the skin of the patient. This striking is not sufficient to cause discomfort or otherwise even a slight damage to the skin of the patient, but is sufficient to startle the patient into a wakeful condition, which is the intent of this apparatus.

USE AND OPERATION OF EMBODIMENT OF FIGS. 6A AND 6B

This collar apparatus is used with or in place of the shoe device of FIGS. 1A, 1B and 1C. The circuit diagrams of FIGS. 2 and 3 anticipate use of either or both stimulators so as to startle the patient into resulting wakefulness. "Wakefulness" is a prime purpose of the monitor. This neck device is adapted to have the electrical signals fed through wires 91 and 92 to the inside of the U-shaped member 94. The portions 96 are anticipated to be tubular and to have positioning as to arcuate shape. There are several tubular members that have bending properties and with the ability to retain a formed shaped arc. No patentable distinction is ascribed to this property.

Motors 93 are secured at the distal end of each member 96. These motors revolve at a selected speed and are actuated only in response to power supplied from the converter. The eccentric 99 may and does produce vibrations and may include a flail 100, which is a very flexible plastic or fabric strip. The rotation of the eccentric and the attached flail is intended to startle the patient into waking up. This may or may not produce crying, but at least the patient is awakened. Inattention to the monitor by the attendant or possible incapacity of the attendant is therefore bypassed.

CIRCUIT DIAGRAM OF FIG. 7

The circit used to actuate the foot apparatus of FIGS. 1A, 1B and 1C and the neck device of FIGS. 6A and 6B may be actuated by a pneumatic flow. Of course, pressurized air may be used to actuate a pneumatic motor, but such motors are usually more expensive than electrical motors. As to be disclosed later, it is anticipated that a plunger mechanism may be used. The use of pressurized air is very desirable where oxygen or like gases are present in the surrounding environment.

In this diagram, an apnea monitor 40, as identified in FIGS. 2 and 3, receives a signal from a patient 102 through a conducting means 104. From this monitor an actuating signal is sent through a conductor 106 to a pneumatic supply unit 108. This supply unit may have a valve to cause a pulsation in the supply conduit 110 or, if pneumatic motors are utilized, a determined pressure supply. This conduit is depicted as supplying pressurized air to a foot apparatus 112 and/or to a neck arrangement 114. It is to be realized that the monitor 40 must be actuated before the pneumatic supply is caused to release pressurized air to these components. The supply 108 may be a storage container or may be a pump. If a pump, the supply may be remotely located. Also depicted is an audible alarm 116 which may be a loudspeaker or a pneumatic horn. This alarm may also be remote from other devices so that an alarm may be sent to another station. Valve actuation to stop and start the flow of air to the stimulators is a matter of selection.

EMBODIMENT OF FIG. 8

Figure 8:
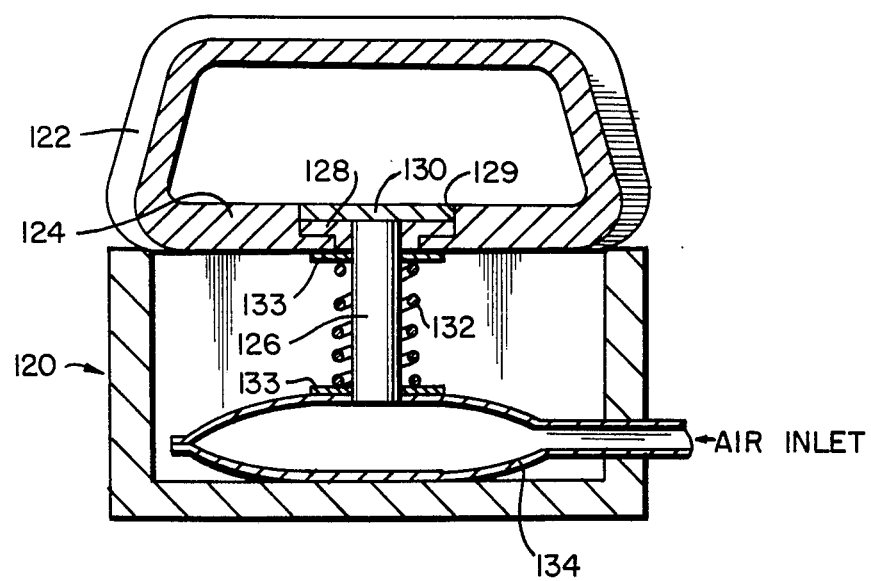
FIG. 8 represents a sectional side view of a pneumatically actuated stimulator for use with the shoe as shown in FIG. 1C, and FIGS. 9A and 9B represent face and side views of the ends of the neck apparatus of FIG. 6A, but with the ends thereof having pneumatic stimulatiors very similar to that of FIG. 8.

In FIG. 8, the shoe 20 of FIGS. 1A, 1B and 1C is contemplated to be utilized but, rather than a rotary stimulation, a reciprocating plunger apparatus is employed. As depicted, a shoe 120, having an upper portion 122 and adapted to be laced into position, has a fixed sole portion 124. As schematically depicted, a reciprocated plunger 126 is carried in a sleeve housing 128 in an aperture 129 formed in this sole member portion 124. This assembly is usually with a rivet crimp or the like. This plunger is provided with a soft tip or is adapted to strike a resilient member 130 adapted to engage the sole of the patient's foot. A spring 132 is shown and is adapted to return the plunger 126 to its retracted position. A washer 133 may be disposed at the top edge of a diaphragm 134 to prevent undue wear. The top end of spring engages housing 128 or another washer 133 disposed to engage the underside of sole 124. This plunger may be moved up and down by a diaphragm device 134 which is moved to the expanded condition by pressurized air.

Plunger securing means is well known and many variations may be made by the designer of the apparatus. If the plunger is caused to touch the bottom of the patient's foot, it would pass through an aperture 136 and, if the plunger were to strike the bottom surface of resilient member 130, securing means for this member must also be provided.

USE AND OPERATION OF EMBODIMENT OF FIG. 8

The shoe sole 124 is provided with an aperture 129 which may be counterbored to provide a smooth seating. The inflow of pressurized air causes diaphragm 134 to expand to cause plunger 126 to move upwardly and move resilient member 130 a small distance upwardly. After pressure has been reduced, the spring 132 causes the diaphragm 134 and the attached plunger 126 to move downward. Plunger 126 is retained by the diaphragm 134 so as to be moved therewith.

EMBODIMENT OF FIGS. 9A AND 9B

Figure 9A:
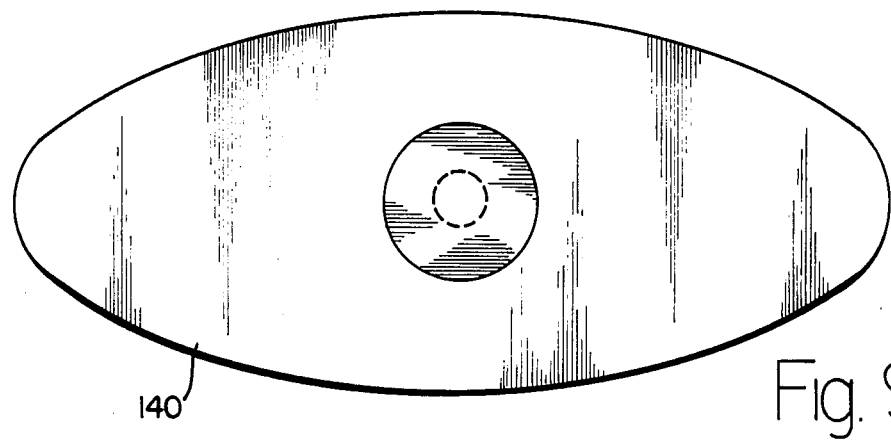
Figure 9B:
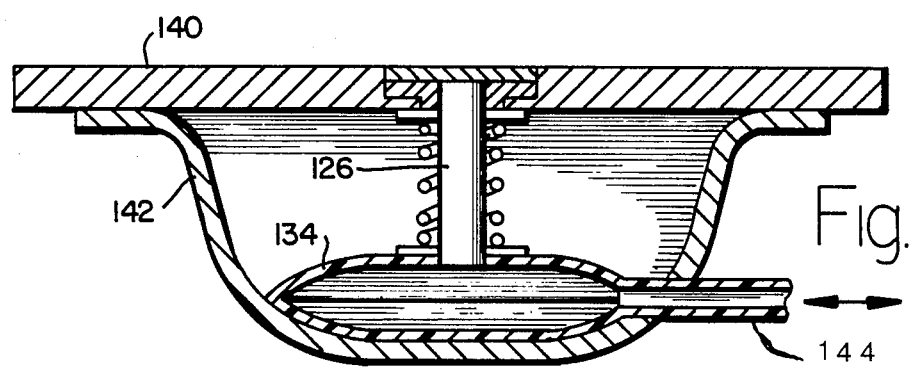
Figure 7:
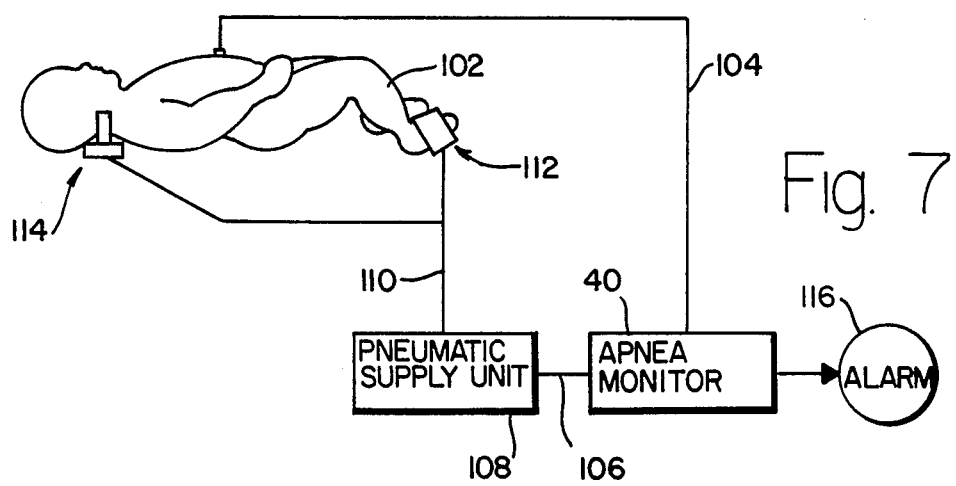
FIG. 7 represents a schematic view of a pneumatic circuit for actuating stimulations to both a foot and the neck portions of a patient.

Still referring to the drawings, and in particular to the diagrammatic showing of FIGS. 9A and 9B, there is shown the neck apparatus of FIGS. 6A and 6B altered to use pneumatically-actuated stimulation rather than electric motor means. As the reciprocating plunger apparatus as in FIG. 8 may also be employed in the neck apparatus, in FIG. 9A (a face view) and FIG. 9B there is a showing of a suggested internal construction. Rather than a sole portion 124 as in FIG. 8, this embodiment provides a flexible retaining member 140 which may be ovoid in configuration. A plunger 126 is similar to identical to the plunger of FIG. 8. A small housing 142 is provided at the rear of the face of retaining member 140. A spring 132, washer 133 and a diaphragm 134 are as in FIG. 8 described above. A sleeve housing 128 and an apeture 129 are also similar to those shown in FIG. 8. An air inlet 144 is shown as connected to the diaphragm from the rear, but may be from the side of the housing 140. This is merely a matter of selection.

The reciprocating plunger 126 is carried in a housing 142 which is disposed at each end of the stimulating apparatus as provided for the neck area of the patient. As in FIGS. 6A and 6B, it is anticipated that the ends of this apparatus may be tied together and, for retention in a desired position, retaining member 140 may also be secured by adhesive means in the form of tape in which the adhesive does not affect the skin of a patient. The securing of this apparatus to the patient is a matter of selection and preference.

In the embodiments of FIGS. 8, 9A and 9B, it is noted that movement of pin 126 is in response to pressurized air input and withdrawal. The diaphragm 134 may be with a single-cup or a dual-cup structure. Diaphragm structures are well known and particularly are used with pressurized fluid for translation into linear motion. In this monitor-assist apparatus, it is contemplated that the pin be secured to the diaphragm so as to be movable with the inflow of pressurized air. No patentable distinction is ascribed to the design of the diaphragm as this is a matter of selection. Valve actuation to produce pulsation of the pressurized air is also well known.

It is believed that the above-shown and -described assist provides a basis for a method of utilizing an apnea monitor to provide actuation for an assist apparatus and for providing a physical stimulation of a patient in response to the monitor's reaction to a reduced respiratory action by the patient, said action of sufficient magnitude to actuate said motor, and in response to a signal from said monitor the assist is also actuated, this method providing added stimulation absent presence and participation of an attendant, this method including the steps of:

receiving a signal from an actuated monitor and converting said received signal into a flow of energy to a stimulation means;

removably attaching a shoe to the foot of a patient and providing said shoe with a selectable tightening means of side portions, said shoe having a sole member which is attached to the side portions and forming and attaching to said sole an enclosure and securing within said enclosure a stimulation device and actuating this stimulation device when the monitor is actuated, and conducting signals from a converter to said sole stimulation device to actuate said stimulations to the patient.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the monitor-assist apparatus may be constructed or used.

While particular embodiments of the apparatus have been shown and described, it is to be understood that the invention is not limited thereto and protection is sought to the broadest extent the prior art allows.

What is claimed is:

1. An apnea monitor-assist apparatus which provides physical stimulation of a patient in response to the monitor's reaction to a reduced respiratory action by the patient, said respiratory action of sufficient magnitude to actuate said monitor-assist and, in response to an electronic signal or signals from said monitor-assist, the assist apparatus is also actuated, said assist apparatus including:
   (a) means for receiving a signal from an actuated monitor and electronically converting said received signal into an electrical flow of current to an electrical motor;
   (b) a shoe removably attachable to a foot of a patient, said shoe characterized as having:
      (b 1) a selectable tightening means;
      (b 2) a sole member;
      (b 3) an upper portion attached to said sole member and, with said upper portion attached to the sole member, said selectable tightening means may be manipulated to cause the shoe to be attached to the foot of the patient, and
      (b 4) an enclosure removably attached to the sole member of the shoe;
         (bb 1) an electric motor arrayed within this enclosure and fixedly secured in spaced array from said sole;
         (bb 2) a shaft within said motor and extending therefrom;
         (bb 3) a disc eccentrically and securely mounted on said shaft and, when said motor is actuated so that the shaft is rotated, the eccentrically mounted disc is also rotated to cause vibration forces to be transmitted to the shoe and patient;
   (c) a converter adapted to change electronic signals from said actuated monitor to electric current, and
   (d) wire conducting means for transmitting electrical current from said converter to said motor in the enclosure portion of the shoe.

2. A monitor-assist apparatus as in claim 1 in which the sole member of the shoe is also formed with an aperture and the eccentric disc also has an attached flail-like flexible member portion which brushes the sole of the foot of a patient when and as the motor is revolved.

3. A monitor-assist apparatus as in claim 1 in which additional stimulation is provided by a U-shaped collar member which is selectively secured to the neck area of a patient and characterized as having an electrical motor disposed in each terminal end of the collar member, with each motor having a shaft on which is secured an eccentric disc and, when the motors are caused to be rotated, the eccentric discs produce vibration forces which are transmitted to the patient, the motors in this collar member being actuated in response to a flow of electric current through said wire conductors to said motors.

4. A monitor-assist apparatus as in claim 3 in which the converter changes the voltage as received from the monitor to a different voltage useful for actuation of the motors.

5. A monitor-assist apparatus as in claim 3 in which the converter changes audio frequency signals into electrical signals and energy to cause electrical current to flow to the motors which are actuated.

6. A monitor-assist apparatus as in claim 3 in which the converter is a plug-in type.

7. A monitor-assist apparatus as in claim 3 in which the converter is disposed within an in-line conductor.

8. A monitor-assist apparatus as in claim 3 in which each eccentric disc carried by the two motors in the U-shaped collar member also is provided by very flexible flail-like portions that brush the skin of the patient when this U-shaped collar is carried by the patient.

9. An apnea monitor-assist apparatus which provides physical stimulation of a patient in response to the monitor's reaction to a reduced respiratory action by the patient, said action of sufficient magnitude to actuate said monitor, and in response to a signal from said monitor the assist is also actuated, said assist including:
   (a) means for receiving a signal from an actuated monitor and converting said received signal into an electrical flow of current to an electrical motor;
   (b) a U-shaped collar member having two terminal ends, which U-shaped collar member is selectively secured to the neck area of a patient, this U-shaped collar member having an electrical motor in each terminal end, and with each motor having a shaft on which is secured an eccentric disc so that when the motors are caused to be rotated, the rotating disc produces vibration forces which are transmitted to the patient, the motors in this collar member being actuated in response to electrical signals derived from said actuated monitor;
   (c) a converter adapted to change electronic signals to an electric current and transmit said signals, and
   (d) wire conducting means for transmitting said electrical current by the wire conducting means from said converter to said motors positioned in the distal terminal ends of said U-shaped collar member.

10. A monitor-assist apparatus as in claim 9 in which each eccentric disc carried by the two motors in the U-shaped collar member also is provided by very flexible flail-like portions that brush the skin of the patient when this U-shaped collar is carried by the patient.

11. An apnea monitor-assist apparatus which provides physical stimulation of a patient in response to the monitor's reaction to a reduced respiratory action by the patient, said regulatory action of sufficient magnitude to actuate said monitor-assist and, in response to an electronic signal or signals from said monitor, the assist apparatus is also actuated, said assist apparatus including:
   (a) means for receiving a signal from an actuated monitor and converting said electronically received signal into an electrical flow of current to an electrical motor;
   (b) a shoe removably attachable to a foot of a patient, said shoe characterized as having:
      (b 1) a selectable tightening means;
      (b 2) a sole member;
      (b 3) an upper portion attached to said sole member and, with said upper portion attached to the sole member, said tightening means may be manipulated to cause the shoe to be attached to the foot of the patient, and
      (b 4) an enclosure removably attached to the sole member of the shoe;
         (bb 1) an aperture formed in and through said sole member of said shoe;
         (bb 2) a diaphragm-type, pneumatically-actuated pin portion carried within the removable enclosure to said sole member and disposing said pin for reciprocating motion and, in response to an electronic signal from said monitor
         (bb 3) a supply source of pressurized air is fed to the diaphragm;
   (c) tubular conducting means for transmitting pressurized air from said supply source to said diaphragm, and
   (d) means for causing pulsations in said pressurized air so as to feed this pressurized air in a pulsating manner to said diaphragm to cause the pin to lightly engage the sole of the patient's foot.

12. A monitor-assist apparatus as in claim 11 in which there is additionally provided a U-shaped collar portion disposed to be removably attached to and around the neck of a patient, said collar portion having the two end portions thereof, each with a flexible flange portion, and an enclosure within which is secured a diaphragm-type pneumatically-actuated pin portion that is disposed for reciprocating motion and, in response to a signal, a supply of pressurized air is fed in a pulsating manner to said diaphragm to effect stimulation to the neck areas of the patient.

13. A monitor-assist apparatus as in claim 12 in which the flexible flange portions have the enclosure intermediate thereof and this enclosure is constructed so as to provide an air inlet means to the diaphragm structure.

14. An apnea monitor-assist apparatus which provides physical stimulation of a patient in response to the monitor's reaction to a reduced respiratory action by the patient, said respiratory action of sufficient magnitude to actuate said monitor-assist and, in response to an electronic signal or signals from said monitor-assist, the assist apparatus is also actuated, said assist apparatus including:
   (a) means for receiving a signal from an actuated monitor and converting electronically received signal into an electrical flow of current to an electrical motor;
   (b) a shoe removably attachable to a foot of a patient, said shoe characterized as having:
      (b 1) a selectable tightening means;
      (b 2) a sole member;
      (b 3) an upper portion attached to said sole member and, with said upper portion attached to the sole member, the said selectable tightening means may be manipulated to cause the shoe to be attached to the foot of the patient;
      (b 4) an enclosure removably attached to the outer surface of the sole member of the shoe, and
         (bb 1) a pneumatic motor arrayed within this enclosure and fixedly secured in spaced array from said sole member;
         (bb 2) a shaft within said motor and extending therefrom;
         (bb 3) a disc eccentrically and securely mounted on said shaft and, when said pneumatic motor is actuated so that the shaft is rotated, the eccentrically mounted disc is also rotated to cause vibration forces to be transmitted to the shoe and patient, and
   (c) tubular conducting means for carrying pressurized air to said motor in the enclosure portion of the shoe.

15. A monitor-assist apparatus as in claim 14 in which additional stimulation is provided by a U-shaped collar member which is selectively secured to the neck area of a patient and characterized as having a pneumatic motor disposed in each terminal end of the collar member, with each motor having a shaft on which is secured an eccentric disc and, when the motors are caused to be rotated, the eccentric discs produce vibration forces which are transmitted to the patient, the motors in this collar member being actuated in response to signals from said converter to said motors.

16. A method of utilizing an apnea monitor to provide actuation of an assist apparatus and for providing a physical stimulation of a patient in response to the monitor's reaction to a reduced respiratory action by the patient, said action of sufficient magnitude to actuate said motor and, in response to a signal from said monitor, the assist is also actuated, this method providing added stimulation absent presence and participation of an attendant, this method including the steps of:
   (a) receiving a signal from an actuated monitor and converting said received signal into a flow of energy to a stimulation means;
   (b) providing a converter which changes electrical signals from the monitor to electrical current;
   (c) removably attaching a shoe to the foot of a patient and providing said shoe with a selectable tightening means of side portions, said shoe having a sole member which is attached to the side portions, and forming and attaching to said sole an enclosure, and securing within said enclosure a stimulation device and actuating this stimulation device when the monitor is actuated, and
   (d) conducting electrical current through wires to said sole stimulation device to actuate said stimulations to the patient.

17. A method of utilizing a monitor as in claim 16 which includes the further step of providing additional stimulation through a U-shaped collar member and providing selective securing means for retaining said collar member to the neck area of a patient, with said additional stimulation provided at each end of the collar member and said additional stimulation actuated in response to signals from the actuated monitor.

18. A method of utilizing a monitor as in claim 17 which includes the further step of causing said stimulations to be provided by electrical motors and electronic signals, all electronic signals being sent through conducting wiring.

19. A method of utilizing a monitor as in claim 17 which includes the further step of causing said stimulations to be provided by pneumatic means and with and by pressurized air sent through tubular conductors to said stimulators.

* * * * *